US011986447B2

(12) United States Patent
Zhuk et al.

(10) Patent No.: US 11,986,447 B2
(45) Date of Patent: *May 21, 2024

(54) METHODS SUITABLE FOR THE TREATMENT OF ACNE

(71) Applicant: Johnson & Johnson Consumer Inc., Skillman, NJ (US)

(72) Inventors: Aliaksandr Zhuk, Warrington, PA (US); Anthony Geonnotti, Princeton, NJ (US); Dara Miller, Skillman, NJ (US); Jennifer Li, Federal Way, WA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 90 days.

This patent is subject to a terminal disclaimer.

(21) Appl. No.: 17/400,721

(22) Filed: Aug. 12, 2021

(65) Prior Publication Data

US 2022/0047544 A1 Feb. 17, 2022

Related U.S. Application Data

(60) Provisional application No. 63/065,069, filed on Aug. 13, 2020.

(51) Int. Cl.
| | | |
|---|---|---|
| *A61K 31/192* | (2006.01) | |
| *A61K 9/00* | (2006.01) | |
| *A61K 31/19* | (2006.01) | |
| *A61K 31/366* | (2006.01) | |
| *A61K 31/7004* | (2006.01) | |
| *A61K 47/10* | (2017.01) | |
| *A61K 47/32* | (2006.01) | |
| *A61P 17/10* | (2006.01) | |

(52) U.S. Cl.
CPC .......... *A61K 31/192* (2013.01); *A61K 9/0014* (2013.01); *A61K 31/19* (2013.01); *A61K 31/366* (2013.01); *A61K 31/7004* (2013.01); *A61K 47/10* (2013.01); *A61K 47/32* (2013.01); *A61P 17/10* (2018.01); *A61K 2300/00* (2013.01)

(58) Field of Classification Search
CPC .... A61K 31/192; A61K 9/0014; A61K 31/19; A61K 31/366; A61K 31/7004; A61K 47/10; A61K 47/32; A61K 2300/00
See application file for complete search history.

(56) References Cited

U.S. PATENT DOCUMENTS

| | | | |
|---|---|---|---|
| 3,035,004 A | 5/1962 | Glavis | |
| 3,931,089 A | 1/1976 | Karl | |
| 4,105,782 A | 8/1978 | Yu | |
| 5,292,843 A | 3/1994 | Jenkins et al. | |
| 6,897,253 B2 | 5/2005 | Schmucker-Castner et al. | |
| 7,288,616 B2 | 10/2007 | Tamareselvy et al. | |
| 10,071,103 B2 * | 9/2018 | Sengupta | A61K 9/10 |
| 10,849,845 B2 | 12/2020 | Verdu et al. | |
| 2006/0270563 A1 | 11/2006 | Yang et al. | |
| 2020/0030202 A1 * | 1/2020 | Chen | A61K 8/8152 |
| 2020/0054654 A1 | 2/2020 | Dolai et al. | |

FOREIGN PATENT DOCUMENTS

| | | |
|---|---|---|
| EP | 0816403 A2 | 1/1998 |
| EP | 1069142 A1 | 1/2001 |
| EP | 1116733 A1 | 7/2001 |
| KR | 20180105998 A | 10/2018 |

OTHER PUBLICATIONS

Kantikosum et al., 12 Clin Cosmet Investig Dermatol. 151-161 (2019) (Year: 2019).*
Garofalo et al., 12 Clin Cosmet Investig Dermatol. 363-369 (May 15, 2019) (Year: 2019).*
(Skin Feel Agents, by G Zocchi) in Handbook of Cosmetic Science and Technology (edited by A. Barel, M. Paye and H. Maibach, Published in 2001 by Marcel Dekker, Inc New York, N.Y.) Chapter 35, pp. 399-415.
(Classification of surfactants, by L. Oldenhove de Guertechin) in Handbook of Cosmetic Science and Technology (edited by A. Barel, M. Paye and H. Maibach, Published in 2001 by Marcel Dekker, Inc., New York, N.Y.) Chapter 37, pp. 431-450.
Holmberg, A. et al. "Biofilm Formation by Propionacterium acnes is a Characteristic of Invasive Isolates. Clin Microbiol Infect 2009; 15: 787-795."
Mintel Database—"Facial Serum" XP055859296, Accession No. 7163517—Jan. 28, 2020.
Mintel Database—"Daily Peel Cleanser" XP055840463, Accession No. 7522385—Apr. 27, 2020.
Mintel Database—"Milk Toning Peel Plus+ Program" XP055859291—Accession No. 6851369—Sep. 10, 2019.
Mintel Database—"Glycolic Acid + Niacinamide Anti-Dark Spot Concentrate" XP055859294—Accession No. 7001123—Nov. 15, 2019.
International Search Report, Appln. No. PCT/IB2021/057485; dated Nov. 24, 2021.

* cited by examiner

*Primary Examiner* — Timothy R Rozof
(74) *Attorney, Agent, or Firm* — Rachel Chaves

(57) ABSTRACT

Provided are methods and compositions suitable for treating acne, disrupting a biofilm, and/or killing bacteria contained in a biofilm. Certain methods comprise contacting skin in need of such treatment with a composition comprising two alpha hydroxy acids and a polyhydroxy acid.

10 Claims, No Drawings

METHODS SUITABLE FOR THE TREATMENT OF ACNE

FIELD OF THE INVENTION

Aspects of the present invention generally pertain to compositions suitable for the treatment of acne, and particularly to compositions comprising alpha hydroxy acids and polyhydroxy acids.

BACKGROUND OF THE INVENTION

Acne disorders are often classified as noninflammatory or inflammatory types. Noninflammatory acne is characterized by closed comedones (whiteheads) and open comedones (blackheads), consisting of compact masses of keratin, sebum, and bacteria, which dilate the follicular duct. A comedone forms when a pilo-sebaceous duct is obstructed and/or when there is increased production of sebum by a sebaceous gland. Formation of the comedone can be followed by inflammation, resulting from bacterial proliferation and/or overproduction of sebum. Typically, the bacteria are anaerobic bacteria such as *Cutibacterium acnes* (formerly *Propionibacterium acnes*). Inflammatory acne is characterized by papules (pimples), pustules, and nodulocystic lesions, which may lead to scarring. Several factors are believed to play important roles in the pathogenesis of acne including: sebum production, hormonal stimulation, plugged pores, and skin pathogens. Sebum levels are increased in subjects with acne by approximately 70% compared to sebum levels of control subjects.

Many treatments and products have been attempted to treat acne, but there is still an ongoing need to additional treatments, as no one treatment has been found to be universally effective. Additionally, there is an ongoing need to identify acne treatments which are not only efficacious but are also well-tolerated by the skin.

SUMMARY OF THE INVENTION

One aspect of the invention pertains to a composition for the treatment of acne comprising:
a. about 0.1 wt. % to about 7.5 wt. % glycolic acid;
b. about 0.1 wt. % to about 5 wt. % gluconolactone;
c. about 0.1 wt. % to about 5 wt. % mandelic acid
d. a glycol;
e. a salt-tolerant thickening polymer,
wherein the total amount of glycolic acid, gluconolactone and mandelic acid is less than about 15 wt. % of the total composition. In one or more embodiments, the total amount of glycolic acid, gluconolactone and mandelic acid is at least about 2 wt. % of the total composition. In some embodiments, the glycol is selected from the group consisting of glycerin, propylene glycol, butylene glycol, pentylene glycol, hexylene glycol, polyethylene glycol, polypropylene glycol, diethylene glycol, triethylene glycol, caprylyl glycol, glycerol, butanediol and hexanetriol, and copolymers and combinations thereof. In one or more embodiments, the composition is in the form of a lotion. In one or more embodiments, the composition is in the form of a lotion. In one or more embodiments, the composition is in the form of a gel. In some embodiments, the composition has a rheometer viscosity of from about 2,000 to about 18,000 cPs at 22° C. In one or more embodiments, the composition has a rheometer viscosity of from about 8,000 to about 10,000 cPs at 22° C. In some embodiments, the composition has a pH of about 3 to about 5. In one or more embodiments, wherein the composition further comprises about 0.5 wt. % to about 5 wt. % salicylic acid. In some embodiments, the composition is substantially free of salicylic acid. In one or more embodiments, the composition is substantially free of lactic acid. In some embodiments, the salt-tolerant thickening polymer comprises sulfonate, acrylate and/or cellulose moieties. In one or more embodiments, the salt-tolerant thickening polymer is selected from the group consisting of polyacrylate crosspolymer-6, hydroxyethyl acrylate/sodium acryloyldimethyl taurate copolymer and combinations thereof. In some embodiments, the salt-tolerant thickening polymer comprises hydroxyethylcellulose.

Another aspect of the invention pertains to a composition for the treatment of acne comprising:
a. about 2.5 wt. % to about 7.5 wt. % glycolic acid;
b. about 1 wt. % to about 5 wt. % gluconolactone;
c. about 1 wt. % to about 5 wt. % mandelic acid
d. about 2.5 wt. % to about 7.5 wt. % propylene glycol;
e. about 0.5 wt. % to about 2 wt. % polyacrylate crosspolymer-6; and
f. about 0.5 wt. % to about 2 wt. % hydroxyethyl acrylate/sodium acryloyldimethyl taurate copolymer,
wherein the total amount of glycolic acid, gluconolactone and mandelic acid is less than about 12 wt. % of the total composition. In one or more embodiments, the composition is in the form of a lotion. In one or more embodiments, the composition is in the form of a gel. In some embodiments, the composition has a rheometer viscosity of from about 2,000 to about 18,000 cPs at 22° C. In one or more embodiments, the composition has a rheometer viscosity of from about 8,000 to about 10,000 cPs at 22° C. In some embodiments, the composition has a pH of about 3 to about 5. In one or more embodiments, wherein the composition further comprises about 0.5 wt. % to about 5 wt. % salicylic acid. In some embodiments, the composition is substantially free of lactic acid.

Another aspect of the invention pertains to a method of treating acne, the method comprising: contacting skin in need of such treatment with a composition comprising a first alpha hydroxy acid, a second alpha hydroxy acid, and a polyhydroxy acid. In one or more embodiments, the first alpha hydroxy acid comprises glycolic acid, the second hydroxy acid comprises mandelic acid, and the polyhydroxy acid comprises gluconolactone. In some embodiments, the total amount of glycolic acid, gluconolactone and mandelic acid is less than about 15 wt. % of the total composition. In one or more embodiments, the total amount of acid in the composition is less than about 15 wt. % of the total composition. In some embodiments, the composition is left on the skin. In one or more embodiments, the composition is in the form of a lotion. In some embodiments, the composition has a pH of about 3 to about 5. In one or more embodiments, the composition further comprises a glycol selected from the group consisting of glycerin, propylene glycol, butylene glycol, pentylene glycol, hexylene glycol, polyethylene glycol, polypropylene glycol, diethylene glycol, triethylene glycol, caprylyl glycol, glycerol, butanediol and hexanetriol, and copolymers and combinations thereof. In some embodiments, the composition is substantially free of lactic acid. In one or more embodiments, the composition is substantially free of salicylic acid.

Another aspect of the invention pertains to a method of treating acne, the method comprising contacting skin in need of such treatment with a composition comprising:
a. about 0.1 wt. % to about 7.5 wt. % glycolic acid;
b. about 0.1 wt. % to about 5 wt. % gluconolactone;
c. about 0.1 wt. % to about 5 wt. % mandelic acid d. a glycol;

e. a salt-tolerant thickening polymer, wherein the total amount of glycolic acid, gluconolactone and mandelic acid is less than about 15 wt. % of the total composition. In some embodiments, the total amount of acid in the composition is less than about 15 wt. % of the total composition. In one or more embodiments, the composition is left on the skin. In some embodiments, the composition is in the form of a lotion. In one or more embodiments, the composition has a pH of about 3 to about 5. In some embodiments, the composition further comprises a glycol selected from the group consisting of glycerin, propylene glycol, butylene glycol, pentylene glycol, hexylene glycol, polyethylene glycol, polypropylene glycol, diethylene glycol, triethylene glycol, caprylyl glycol, glycerol, butanediol and hexanetriol, and copolymers and combinations thereof. In one or more embodiments, the composition is substantially free of lactic acid. In some embodiments, the composition is substantially free of salicylic acid. In one or more embodiments, the salt-tolerant thickening polymer comprises acrylate and/or cellulose moieties. In some embodiments, the salt-tolerant thickening polymer is selected from the group consisting of polyacrylate crosspolymer-6, hydroxyethyl acrylate/sodium acryloyldimethyl taurate copolymer and combinations thereof.

Another aspect of the invention pertains to a method of disrupting a biofilm or killing bacteria contained in a biofilm, the method comprising: applying to a surface having a biofilm a composition comprising a first alpha hydroxy acid, a second alpha hydroxy acid, and a polyhydroxy acid. In one or more embodiments, the surface is a surface on skin. In some embodiments, the skin has acne. In one or more embodiments, the biofilm contains *Cutibacterium acnes* bacteria. In some embodiments, the first alpha hydroxy acid comprises glycolic acid, the second hydroxy acid comprises mandelic acid, and the polyhydroxy acid comprises gluconolactone. In one or more embodiments, the total amount of glycolic acid, gluconolactone and mandelic acid is less than about 15 wt. % of the total composition. In some embodiments, the total amount of acid in the composition is less than about 15 wt. % of the total composition. In one or more embodiments, the composition is in the form of a lotion. In some embodiments, the composition has a pH of about 3 to about 5. In one or more embodiments, the composition further comprises a glycol selected from the group consisting of glycerin, propylene glycol, butylene glycol, pentylene glycol, hexylene glycol, polyethylene glycol, polypropylene glycol, diethylene glycol, triethylene glycol, caprylyl glycol, glycerol, butanediol and hexanetriol, and copolymers and combinations thereof. In some embodiments, the composition is substantially free of lactic acid. In one or more embodiments, the composition is substantially free of salicylic acid.

Another aspect of the invention pertains to a method of disrupting a biofilm or killing bacteria contained in a biofilm, applying to a surface having a biofilm a composition comprising:

a. about 0.1 wt. % to about 7.5 wt. % glycolic acid;

b. about 0.1 wt. % to about 5 wt. % gluconolactone;

c. about 0.1 wt. % to about 5 wt. % mandelic acid d. a glycol;

e. a salt-tolerant thickening polymer, wherein the total amount of glycolic acid, gluconolactone and mandelic acid is less than about 15 wt. % of the total composition, wherein the composition has a pH of about 3 to about 5 and wherein the surface is a surface on skin. In some embodiments, the skin has acne. In one or more embodiments, the biofilm contains *Cutibacterium acnes* bacteria. In some embodiments, the total amount of acid in the composition is less than about 15 wt. % of the total composition.

In one or more embodiments, the composition further comprises a glycol selected from the group consisting of glycerin, propylene glycol, butylene glycol, pentylene glycol, hexylene glycol, polyethylene glycol, polypropylene glycol, diethylene glycol, triethylene glycol, caprylyl glycol, glycerol, butanediol and hexanetriol, and copolymers and combinations thereof. In some embodiments, the composition is substantially free of lactic acid. In one or more embodiments, the composition is substantially free of salicylic acid. In some embodiments, the salt-tolerant thickening polymer is selected from the group consisting of polyacrylate crosspolymer-6, hydroxyethyl acrylate/sodium acryloyldimethyl taurate copolymer and combinations thereof.

DETAILED DESCRIPTION OF THE INVENTION

Definitions

What is meant by "treating acne" is reducing or preventing acne or rosacea.

What is meant by a "product" is a product in finished packaged form. In one embodiment, the package is a container such as a plastic, metal or glass tube or jar containing the composition. The product may further contain additional packaging such as a plastic or cardboard box for storing such container. In one embodiment, the product contains instructions directing the user to apply the composition to (i) treat acne or (ii) reduce the appearance of oil or pores on the skin.

What is meant by "promoting" is promoting, advertising, or marketing. Examples of promoting include, but are not limited to, written, visual, or verbal statements made on the product or in stores, magazines, newspaper, radio, television, internet, and the like.

For promoting the treatment of acne, examples of such statements include, but are not limited to, "treats acne," "treating acne," "prevents acne," "reduces acne lesions, comedones, or pimples," "reduces the appearance of acne lesions, comedones, or pimples," "reduces the appearance of acne breakouts and blemishes," "preventing, controlling or regulating the appearance of acne breakouts and blemishes", and "reduces breakouts and blemishes."

For promoting the reduction in the appearance of oil on the skin, examples of such statements include, but are not limited to, "reduces the appearance of sebum," "preventing, controlling or regulating the production of sebum," "reduces sebum," "reduces the appearance of oily/shiny skin," "reduces the appearance of greasy skin," and "reduces shine on the skin, hair, or scalp." In one embodiment, the composition is applied to skin not in need of treatment for acne (i.e., skin not suffering from acne or the scalp/hair).

For promoting the reduction in the appearance of pores on the skin, examples of such statements include, but are not limited to, "reduces the size of pores," "minimizes the appearance of pores," "refines the appearance of pores," "reduces the visibility or pores," and "closes pore opening." In one embodiment, the composition is applied to skin not in need of treatment for acne (i.e., skin not suffering from acne).

As used herein, "administering to skin" or "contacting the skin" means contacting (e.g., by use of the hands or an applicator such, but not limited to, a wipe, tube, roller, spray, or patch) the area of skin in need such treatment or an area of skin proximate to the area of skin in need of such treatment.

As used herein, "composition" means a composition suitable for topical administration to the skin.

As used herein, "cosmetically-acceptable" means that the ingredients which the term describes are suitable for use in contact with the skin without undue toxicity, incompatibility, instability, irritation, allergic response, and the like.

As used herein, "safe and effective amount" means an amount of the compound, carrier, or of the composition sufficient to induce an enhancement in tissue elasticity, but low enough to avoid undesirable detrimental adverse side effects. The safe and effective amount of the compounds or composition will vary with the area being treated, the age, health and skin type of the end user, the duration and nature of the treatment, the specific compound or composition administered, the particular cosmetically-acceptable carrier utilized, and like factors.

The articles "a," "an," and "the" all refer to the plural as well as the singular.

The expression "one or more" is synonymous with "at least one" and include individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present disclosure, unless otherwise indicated.

As used herein unless otherwise indicated, "substantially free" or "essentially free" means that there is less than about 2% by weight of a component added to a composition, based on the total weight of the compositions. The compositions may include less than about 1, 0.5, or 0.1 wt. %, or none of the component.

All publications and patent applications cited in this specification are herein incorporated by reference, and for any and all purposes, as if each individual publication or patent application were specifically and individually indicated to be incorporated by reference. The present disclosure controls if there an inconsistency between the present disclosure and any incorporated publications or patents.

Methods, Uses and Compositions

Various aspects of the invention pertain to methods of and compositions suitable for treating acne. In one or more embodiments, the method comprises skin in need of such treatment with a composition comprising two alpha hydroxy acids and a polyhydroxy acid. That is, in some embodiments, the invention pertains to use of composition comprising two alpha hydroxy acids and a polyhydroxy acid for the treatment of acne. It has been surprisingly discovered that the combination of these three acids (and particularly a blend of glycolic acid, gluconolactone and mandelic acid) is effective in the treatment of acne. In particular, it has been surprisingly discovered that these three acids are capable of improving acne conditions (e.g., reducing acne lesions, improve skin texture, increase in skin clarity and evenness, etc.) while being well tolerated by the skin.

Additionally, recent evidence suggests that acne may be related to the formation of biofilms of the skin by certain bacteria (e.g., *Cutibacterium acnes*). Accordingly, another aspect of the invention pertains to a method of disrupting a biofilm or killing bacteria contained in a biofilm. As used herein, the term "disrupting a biofilm" means that at least some of the bacteria in the biofilm are killed such that over time the matrix of the biofilm will degrade or be dispersed or become disorganized. In some embodiments, the matrix of the biofilm may be degraded during or shortly after exposure of the biofilm to one or more of the compositions. The method comprises applying to a surface having a biofilm (e.g., skin afflicted with acne) a composition comprising a first alpha hydroxy acid, a second alpha hydroxy acid, and a polyhydroxy acid. It has been surprisingly discovered that the combination of these three acids (and particularly a blend of glycolic acid, gluconolactone and mandelic acid) is effective in killing *Cutibacterium acnes*. In particular, it has been surprisingly discovered that these three acids are capable of not only killing *Cutibacterium acnes*, but also in disrupting the biofilm formed by *Cutibacterium acnes* or otherwise passing through the biofilm matrix to kill the *Cutibacterium acnes* in the biofilm.

Alpha hydroxy acids are compounds which contain a carboxylic acid that is substituted with a hydroxyl group on the adjacent carbon atom. Examples of alpha hydroxy acids include, but are not limited to, glycolic acid, malic acid, tartaric acid, pyuric acid, mandelic acid, or any combination of any of the foregoing. Each of the alpha hydroxy acids may be present in amounts ranging from about 0.1, 0.2, 0.3, 0.4, 0.5, 0.6, 0.7, 0.8, 0.9, 1.0, 1.5, 2, 2.5, 3, 3.5, 4, 4.5, 5 or 5.5 to about 5, 5.5, 6, 6.5, 7 or 7.5 wt. % of the total composition.

In one or more embodiments, at least one of the alpha hydroxy acids comprises glycolic acid. In some embodiments, at least one of the alpha hydroxy acids comprises mandelic acid. In further embodiments, the composition comprises a blend of glycolic acid and mandelic acid. Glycolic acid is the smallest alpha hydroxy acid, and has molecular formula $C_2H_4O_3$. Glycolic acid, is individually well-known in the art and readily available from a variety of commercial sources. Glycolic acid may be present in the composition in an amount ranging from about 0.1, 0.2, 0.3, 0.4, 0.5, 0.6, 0.7, 0.8, 0.9, 1.0, 1.5, 2, 2.5, 3, 3.5, 4, 4.5, 5 or 5.5 to about 5, 5.5, 6, 6.5, 7 or 7.5 wt. % of the total composition. Mandelic acid is an aromatic alpha hydroxy acid, and has molecular formula $C_6H_5CH(OH)CO_2H$. Mandelic acid is individually well-known in the art and readily available from a variety of commercial sources. Mandelic acid may be present in the composition in an amount ranging from about 0.1, 0.2, 0.3, 0.4, 0.5, 0.6, 0.7, 0.8, 0.9, 1.0 or 1.5 to about 1.5, 2, 2.5, 3, 3.5, 4, 4.5 or 5 wt. % of the total composition.

Polyhydroxy acids are acids with multiple hydroxyl groups that can often act as moisturizers, anti-irritants and humectants. Examples of polyhydroxy acid include, but are not limited to, gluconic acid lactones and aldonic acid lactones such as allonolactone, altronolactone, gluconolactone, glucoheptonolactone, mannolactone, gulonolactone, idonolactone, galactonolactone, talonolactone, lactobionic acid, maltobionic acid, and tartaric acid. In some embodiments, the polyhydroxy acid comprises gluconolactone. Gluconolactone is a polyhydroxy acid having molecular formula $C_6H_{10}O_6$. Gluconolactone is individually well-known in the art and readily available from a variety of commercial sources. The polyhydroxy acid (e.g., gluconolactone) may be present in the composition in an amount ranging from about 0.1, 0.2, 0.3, 0.4, 0.5, 0.6, 0.7, 0.8, 0.9, 1.0 or 1.5 to about 1.5, 2, 2.5, 3, 3.5, 4, 4.5 or 5 wt. % of the total composition.

In one or more embodiments the total amount of the alpha hydroxy acids and polyhydroxy acid is less than about 15, 14.5, 14, 13.5, 13, 12.5, 12, 11 or 10.5 wt. % of the total composition. In some embodiments the total amount of the alpha hydroxy acids and polyhydroxy acids is at least about 2, 2.5, 3, 3.5, 4, 4.5, 5, 5.5, 6, 6.5, 7, 7.5, 8, 8.5, 9, 9.5 or 10 wt. % of the total composition.

In some embodiments, the composition comprises glycolic acid, mandelic acid and gluconolactone as the alpha hydroxy acids and polyhydroxy acid. In one or more embodiments, the total amount of glycolic acid, gluconolactone and mandelic acid is less than about 15, 14.5, 14, 13.5, 13, 12.5, 12, 11 or 10.5 wt. % of the total composition. In some embodiments the total amount of glycolic acid, gluconolactone and mandelic acid is at least about 2, 2.5, 3, 3.5, 4, 4.5, 5, 5.5, 6, 6.5, 7, 7.5, 8, 8.5, 9, 9.5 or 10 wt. % of the total composition.

In some embodiments, the composition further comprises a beta hydroxy acid. Exemplary beta-hydroxy acids include, but are not limited to, salicylic acid, beta-hydroxybutanoic acid, tropic acid, and trethocanic acid. Other suitable beta-hydroxy acids are described in U.S. Pat. No. 5,665,776 (Yu). In some embodiments, the composition comprises salicylic acid as the beta hydroxy acid. When present, the beta hydroxy acid may be present in an amount ranging from about 0.1, 0.2, 0.25, 0.5, 0.75, 1, 1.5, 2, 2.5 or 3 to about 0.5, 0.75, 1, 1.5, 2, 2.5, 3, 4 or 5 wt. %. In some embodiments, salicylic acid may be present in an amount ranging from about 0.1, 0.2, 0.25, 0.5, 0.75, 1, 1.5, 2, 2.5 or 3 to about 0.5, 0.75, 1, 1.5, 2, 2.5, 3, 4 or 5 wt. %.

In one or more embodiments, the composition may comprise less than 0.6, 0.5, 0.4, 0.3, 0.2, 0.1, 0.05 of other acids. In further embodiments, the composition is substantially free or free of (i.e., does not contain) other acids. In one or more embodiments, the composition may comprise less than 0.6, 0.5, 0.4, 0.3, 0.2, 0.1, 0.05 of salicylic acid. In further embodiments, the composition is substantially free or free of (i.e., does not contain) salicylic acid. In one or more embodiments, the composition may comprise less than 0.6, 0.5, 0.4, 0.3, 0.2, 0.1, 0.05 of lactic acid. In further embodiments, the composition is substantially free or free of (i.e., does not contain) lactic acid.

In some embodiments, the total amount of acid in the composition of any kind is less than 15, 14.5, 14, 13.5, 13, 12.5, 12, 11.5, 11, 10.5 or 10 wt. % of the total composition.

In one or more embodiments, the composition further comprises a glycol. While not wishing to be bound to any particular theory, it is thought that the glycol increases bio-delivery of one or more of the acids. In one or more embodiments, the glycol is selected from the group consisting of glycerin, propylene glycol, butylene glycol, pentalene glycol, hexylene glycol, polyethylene glycol, polypropylene glycol, diethylene glycol, triethylene glycol, caprylyl glycol, glycerol, butanediol and hexanetriol, and copolymers and combinations thereof. In further embodiments, the glycol comprises propylene glycol.

In some embodiments, the composition further comprises a salt-tolerant thickening polymer and/or dispersing polymer. As used herein, the term "salt-tolerant thickening polymer" refers to a polymer which increases the viscosity of the composition while still being able to maintain stability in the presence of relatively high concentrations of salts in the formulation. In some embodiments, the salt-tolerant thickening polymer can increase the viscosity of a composition having a salt concentration above about 2.0%. Particularly, the salt-tolerant thickening polymer can withstand relatively high concentrations of salt and function as thickeners at relatively low pH (e.g., less than about 4.5 or 4). As salt comes from ionized form of acids, the salt content is related to pH. Thus, for example, one or more of the compositions described herein are made at pH 3.8-4.0, which is above pKa values of the acids (e.g., mandelic, glycolic, gluconolactone, salicylic, etc.); therefore over 50% of acid exist in the formula as salt. As used herein, the term "dispersing polymer" refers to a polymer which allows for the suspension of particles and/or droplets.

The salt-tolerant thickening polymer may either be cross-linked or not. In one or more embodiments, the salt-tolerant thickening polymer may include polyacrylate-based thickeners, polyacrylamide thickeners, or, cross-linked copolymers containing acrylate and/or acrylamide moieties. In one or more embodiments, the salt-tolerant thickening polymer comprises a sulfonate group. In one or more embodiments, the salt-tolerant thickening polymer includes a a structural unit derived from acrylamidoalkylsulfonic acid or a salt thereof. In such embodiments, the salt-tolerant thickening polymer may include the following:

Polymers based on 2-acrylamido-2-methylpropanesulfonic acid and/or salts thereof, such as those sold under the name Aristoflex™, and are described in EP0816403, EP1116733 and EP1069142.

Polymers based on 2-methyl-2-[(1-oxo-2-propenyl)amino]-1-propanesulfonic acid and/or salts thereof, which are described in U.S. Ser. No. 10/849,845B2.

polymer containing a structure (I):

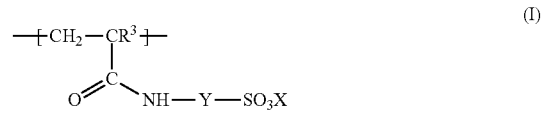

(Wherein, $R^3$ is a hydrogen atom, methyl or ethyl, Y is an alkylene group having 1 to 9 carbon atoms, and X is an ammonium, an alkali metal or an alkaline earth metal ion.) The salt-tolerant thickening polymers may include other neutral and/or hydrophobic monomers.

Suitable neutral monomers include, but are not limited to, N,N-dialkylacrylamides, in which each of the alkyl groups includes between 1 and 4 carbon atoms more particularly denotes N,N-dimethylacrylamide, N,N-diethylacrylamide, N,N-dipropylacrylamide, or N,N-diisopropylacrylamide.

Suitable hydrophobic monomers (also referred to as "associative" monomers) are those used in hydrophobically modified polyelectrolytes are described for example in U.S. Pat. Nos. 5,292,843, 6,897,253, 7,288,616, 3,035,004, and U.S. Patent Publication No. 2006/0270563, the contents each of which is hereby incorporated by reference in their entirety.

A "hydrophobic moiety", as used herein", means a non-polar moiety that contains at least one of the following: (a) a carbon-carbon chain of at least five carbons in which none of the five carbons is a carbonyl carbon or has a hydrophilic moiety bonded directly to it; (b) two or more alkyl siloxy groups (—[Si(R)$_2$—O]—); and/or (c) two or more oxypropylene groups in sequence. A hydrophobic moiety may be, or include, linear, cyclic, aromatic, saturated or unsaturated groups. In certain preferred embodiments, hydrophobic moieties comprise a carbon chain of at least six or more carbons, more preferably seven or more carbons in which none of the carbons in such chain have a hydrophilic moiety bonded directly thereto. Certain other preferred hydrophobic moieties include moieties comprising a carbon chain of about eight or more carbon atoms, more preferably about 10 or more carbon atoms in which none of the carbons in such chain have a hydrophilic moiety bonded directly thereto. Examples of hydrophobic functional moieties may include esters, ketones, amides, carbonates, urethanes, carbamates, or xanthate functionalities, and the like, having incorporated therein or attached thereto a carbon chain of at least four carbons in which none of the four carbons has a hydrophilic moiety bonded directly to it. Other examples of hydrophobic moieties include groups such as poly(oxypropylene), poly(oxybutylene), poly(dimethylsiloxane), fluorinated hydrocarbon groups containing a carbon chain of at least four carbons in which none of the four carbons has a hydrophilic moiety bonded directly to it, and the like.

As used herein, the term "hydrophilic moiety" is any anionic, cationic, zwitterionic, or nonionic group that is polar. Nonlimiting examples include anionics such as: sulfate, sulfonate, carboxylic acid/carboxylate, phosphate, phosphonates, and the like; cationics such as: amino, ammonium, including mono-, di-, and trialkylammonium species, pyridinium, imidazolinium, amidinium, poly(ethyleneiminium), and the like; zwitterionics such as: ammonioalkylsulfonate, ammonioalkylcarboxylate, amphoacetate, and the like; and nonionics: such as hydroxyl, sulfonyl, ethyleneoxy, amido, ureido, amine oxide, and the like.

Specific Examples of hydrophobic monomers include, but are not limited to:

Acrylic hydrophobic monomer according to structure (II):

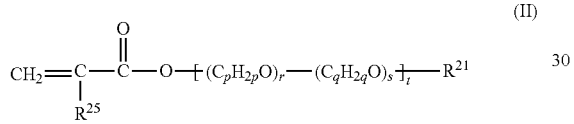

(II)

wherein
$R^{21}$ is linear or branched or cyclic (C5-C50) alkyl, hydroxyalkyl, alkoxyalkyl, aryl, or aralkyl,
$R^{25}$ is H, or methyl, or ethyl, and
p and q are each independently of each other 2, or 3, or 4
r and s are each independently of each other 0-50
t is 1-50.

In one embodiment, the hydrophobic monomer is a compound according to structure II, wherein $R^{21}$ is linear ($C_8$-$C_{20}$) alkyl. In one embodiment, the hydrophobic monomer is a compound according to structure II, wherein p=0 and s=0 and $R^{21}$ is a a linear or branched ($C_8$-$C_{20}$) alkyl group. In one embodiment, the hydrophobic monomer is a compound according to structure II, wherein p=2, s=0, and t=1.

Suitable ethylenically unsaturated hydrophobic monomers include:
alkyl-(meth)acrylates that comprise at least one linear or branched (C5-C40) alkyl-group per molecule, such as pentyl-(meth)acrylates, hexyl-(meth)acrylates, tridecyl-(meth)acrylates, myristyl-(meth)acrylates, cetyl-(meth)acrylates, stearyl-(methyl)acrylates, behenyl polyalkoxylated (meth)acrylates, and mixtures thereof,
alkyl-polyether (meth)acrylates that comprise at least one linear or branched (C5-C40) alkyl-polyether group per molecule, such as hexyl polyalkoxylated (meth)acrylates, tridecyl polyalkoxylated (meth)acrylates, myristyl polyalkoxylated (meth)acrylates, cetyl polyalkoxylated (meth)acrylates, stearyl polyalkoxylated (methyl) acrylates, eicosyl polyalkoxylated (meth)acrylates, behenyl polyalkoxylated (meth)acrylates, melissyl polyalkoxylated (meth)acrylates, tristyrylphenoxyl polyalkoxylated (meth)acrylates, and mixtures thereof,
alkyl-polyether (meth)acrylamides that comprise at least one (C5-C40) alkyl-polyether substituent group per molecule, such as hexyl polyalkoxylated (meth)acrylamides, tridecyl polyalkoxylated (meth)acrylamides, myristyl polyalkoxylated (meth)acrylamides, cetyl polyalkoxylated (meth)acrylamides, stearyl polyalkoxylated (methyl)acrylamides, eicosyl polyalkoxylated (meth)acrylamides, behenyl polyalkoxylated (meth)acrylamides, melissyl polyalkoxylated (meth) acrylamides and mixtures thereof,
alkyl-polyether vinyl esters, alkyl-polyether vinyl ethers, or alkyl-polyether vinyl amides that comprise at least one (C5-C40) alkyl-polyether substituent group per molecule such as vinyl stearate polyalkoxylate, myristyl polyalkoxylated vinyl ether, and mixtures thereof,
as well as mixtures of two or more of any of the above alkyl-polyether acrylates, alkyl-polyether methacrylates, alkyl-polyether acrylamides, alkyl-polyether methacrylamides, alkyl-polyether vinyl esters, alkyl-polyether vinyl ethers, and alkyl-polyether vinyl amides.
cyclohexyl(meth)acrylate, 2-ethylhexyl (meth)acrylate, isodecyl(meth)acrylate, lauryl(meth)acrylate isobornyl (meth)acrylate, benzyl(meth)acrylate, phenoxyethyl (meth)acrylate, tetrahydrofurfuryl(meth)acrylate, glycidyl(meth)acrylate, vinyl 2-ethylhexanoate, and N-tert-octyl(meth)acrylamide.

In one embodiment, the hydrophobic monomer comprises one or more alkyl-polyalkoxylated (meth)acrylates that comprise one linear or branched (C5-C40) alkyl-polyethoxylated group, more typically (C10-C22) alkyl-polyethoxylated group per molecule, such as decyl-polyethoxylated (meth)acrylates, tridecyl-polyethoxylated (meth)acrylates, myristyl-polyethoxylated (meth)acrylates, cetyl-polyethoxylated (meth)acrylates, stearyl-polyethoxylated (methyl)acrylates, eicosyl-polyethoxylated (meth)acrylates, behenyl-polyethoxylated (meth)acrylates, even more typically decyl-polyethoxylated methacrylates, tridecyl-polyethoxylated methacrylates, myristyl-polyethoxylated methacrylates, cetyl-polyethoxylated methacrylates, stearyl-polyethoxylated methylacrylates, eicosyl-polyethoxylated methacrylates, behenyl-polyethoxylated methacrylates, and mixtures thereof.

The salt-tolerant thickening polymer can contain other monomers, for example, ethylenically unsaturated monomers such as acrylamide, dimethyl-acrylamide, and diacetone (meth)acrylamide, vinyl esters such as vinyl acetate, vinyl propionate, N-vinylamides such as: N-vinylpyrrolidione, N-vinylcaprolactam, N-vinylformamide, and N-vinylacetamide, and vinyl ethers such as, methyl vinyl ether, ethyl vinyl ether, butyl vinyl ether, and hydroxybutyl vinyl ether, and ethylenically unsaturated aryl compounds, such as styrene, acetoxyethyl (meth)acrylate, (meth)acrylamides such as, (meth)acrylamide, N-methylol (meth)acrylamide, N-butoxyethyl(meth)acrylamide, N,N-dimethyl (meth)acrylamide, N-isopropyl(meth)acrylamide, N-tert-butyl (meth) acrylamide, and ethylenically unsaturated alkyl esters of dicarboxylic acid monomers, such as butyl methyl maleate, dimethylaminoethyl(meth)acrylate, diethylaminoethyl (meth)acrylate, tert-butylaminoethyl(meth)acrylate.

In one or more embodiments, the salt-tolerant thickening polymer and/or dispersing polymer comprises 2-acrylamido-2-methylpropane sulfonate (also known as AMPS) moieties. In some embodiments, the salt-tolerant thickening polymer comprises ammonium acryloyldimethyltaurate moieties. In one or more embodiments, the acrylate-containing polymer is not a homopolymer of acrylate moieties. In some embodiments, the salt-tolerant thickening polymer comprises polyacrylate crosspolymer-6, hydroxyethyl acrylate/sodium acryloyldimethyl taurate copolymer, sodium acryloyldimethyltaurate/VP crosspolymer, or combinations thereof. Polyacrylate crosspolymer-6 is available as Sepimax Zen™ (INCI name: Polyacrylate crosspolymer-6), which is provided in the form of a powder, sold by Seppic. Hydroxyethyl acrylate/sodium acryloyldimethyl taurate copolymer is available as Sepinov™ EMT10 (INCI name: Hydroxyethyl Acrylate/Sodium Acryloyldimethyl Taurate Copolymer), which is provided in the form of a powder, also sold by Seppic. Acryloyldimethyltaurate/VP Crosspolymer and Ammonium Acryloyldimethyltaurate/VP Copolymer are available as Aristoflex® AVS and Aristoflex® AVC, respectively, from Clariant (INCI name: Sodium Acryloyldimethyltaurate/VP Crosspolymer and Ammonium Acryloyldimethyltaurate/VP Copolymer). Additional information regarding these polymers can be found in the below table.

In further embodiments, the cellulose-containing polymer is a cellulose ether-based polymer. Examples of cellulose-containing polymer include, but are not limited to, hydroxyalkylcellulose, carboxyalkyl cellulose, alkylcellulose, hydroxyalkyl alkylcellulose, cationic hydroxyalkyl cellulose, hydrophobically modified hydroxyalkyl cellulose, or cationic hydrophobically modified hydroxyalkyl cellulose. In further embodiments, the thickening and/or dispersing polymer comprises hydroxyethylcellulose, carboxymethyl cellulose, methylcellulose, hydroxypropyl methylcellulose, ethylcellulose, cationic hydroxyethyl cellulose, hydrophobically modified hydroxyethyl cellulose, or cationic hydrophobically modified hydroxyethyl cellulose.

In some embodiments, thickening polymer is a dispersing polymer. The term "dispersing" polymer means that compositions with such polymers exhibit yield stress. [As used herein, the term "yield value" means that the elastic modulus of the compositions must be higher than the viscous modulus in the low strain/stress plateau region of the amplitude sweep. The yield stress is then taken as the stress at the crossover where $G'=G''$ and expressed in Pascal (Pa). In one or more embodiments, compositions of the present invention Examples of Sulfonate-Containing Polymers

| Tradename | INCI | Description |
|---|---|---|
| Aristoflex® AVC | Ammonium Acryloyldimethyltaurate/ VP Copolymer | Ammonium Acryloyldimethyltaurate/VP Copolymer is a copolymer of Ammonium AMPS (q.v.) and N-Vinyl Pyrrolidone (q.v.) monomers |
| Aristoflex® AVS | Sodium Acryloyldimethyltaurate/ VP Crosspolymer | Sodium AcryloyldimethyltaurateNP Crosspolymer is a copolymer of sodium acryloyldimethyltaurate and N-Vinyl Pyrrolidone (q.v.) crosslinked by 1,1,1-trimethylolpropane triacrylate |
| Aristoflex® BLV | Ammonium Acryloyldimethyltaurate/ Beheneth-25 Methacrylate Crosspolymer | Ammonium Acryloyldimethyltaurate/Beheneth-25 Methacrylate Crosspolymer is a copolymer of Ammonium AMPS (q.v.) and Beheneth-25 Methacrylate (q.v.) monomers. |
| Aristoflex® HMB | Ammonium Acryloyldimethyltaurate/ Beheneth-25 Methacrylate Crosspolymer | Ammonium Acryloyldimethyltaurate/Beheneth-25 Methacrylate Crosspolymer is a copolymer of Ammonium AMPS (q.v.) and Beheneth-25 Methacrylate (q.v.) monomers |
| Aristoflex® Velvet | Polyacrylate Crosspolymer-11 | Polyacrylate Crosspolymer-11 is a polymer of Methacrylic Acid (q.v.), acryloyl dimethyltaurate and Dimethylacrylamide (q.v.), crosslinked with PPG-3 glyceryl triacrylate, and partially neutralized with Ammonia (q.v.). It conforms generally to the formula: |
| Aristoflex® Silk | Sodium Polyacryloyldimethyl Taurate | Sodium Polyacryloyldimethyl Taurate is an anionic polymer from acrylamide alkyl sulfonic acid or salt thereof. |
| Sepinov™ EMT 10 | Hydroxyethyl Acrylate/ Sodium Acryloyldimethyl Taurate Copolymer | Hydroxyethyl Acrylate/Sodium Acryloyldimethyl Taurate Copolymer is a copolymer of sodium hydroxyethyl acrylate and acryloyldimethyl taurate monomers. |
| Sepimax Zen™ | Polyacrylate Crosspolymer-6 | Polyacrylate Crosspolymer-6 is a copolymer of Ammonium AMPS (q.v.), Dimethylacrylamide (q.v.), Lauryl Methacrylate (q.v.) and laureth-4 methacrylate, crosslinked with Trimethylolpropane Triacrylate (q.v.) |

Naturally-derived salt-tolerant thickening polymers include, but are not limited to, cellulose, xanthan, carrageenan, galactomannans, guar, tara, *Cassia, Sesbania*, locust bean gum, gellan gum, welan gum, carob seed flour, guar seed flour, starch, alginates, carrageenan, gellan, pullulan, scleroglucan, schizophyllan, curdlan, diutan, dextran, welan, chitin, and derivatives thereof, particularly derivatives in the form of alkylations (e.g., methyl ethers, ethyl ethers, C12-18 alkyl ethers), hydroxyalkylations (hydroxyethyl, hydroxypropyl or mixed ethers) and carboxymethylation.

In some embodiments, the salt-tolerant thickening polymer and/or dispersing polymer is a cellulose-containing polymer. That is, the polymer comprises cellulose moieties.

exhibit a yield value of about 0.1 Pa or more, or of about 0.5 Pa or more, or of about 1.0 Pa or more, or of about 2.0 Pa or more.

In some embodiments, the pH of the composition ranges from about 3, 3.1, 3.2, 3.3, 3.4, 3.5, 3.6, 3.7, 3.8 or 3.9 to about 3.8, 3.9, 4, 4.1, 4.2, 4.3, 4.4, 4.5, 4.6, 4.7, 4.8, 4.9 or 5. In some embodiments, the pH of the composition ranges from about 3 to about 5, or about 3.5 to about 4.5. Compositions which fall below these pH ranges are considered very acidic for skin, and generally function as chemical peels. Also, chemical peels may have higher concentrations of acids than the embodiments described herein (e.g., as high as 50%), and may have a water-like viscosity.

Any suitable method of applying the composition to the skin in need may be used. For example, the composition may be applied directly from a package to the skin in need, by hand to the skin in need, or may be transferred from a substrate such as a wipe or mask, or a combination of two or more thereof. In other embodiments, the composition may be applied via a dropper, tube, roller, spray, and patch or added to a bath or otherwise to water to be applied to the skin, and the like. The composition may be applied in a variety of manners/forms, including, without limitation, as a leave-on cream, mask, and/or serum. In one or more embodiments, the composition is left on the skin after application. The compositions may be left on for a period of at least 1, 5, 10, 24 or 48 hours.

Exemplary Compositions

Any of the embodiments described herein can be combined in various combinations. Another aspect of the invention pertains to a composition which is suitable for the treatment of acne. In one or more embodiments, the composition comprises:
a. about 0.1 wt. % to about 7.5 wt. % glycolic acid;
b. about 0.1 wt. % to about 5 wt. % gluconolactone;
c. about 0.1 wt. % to about 5 wt. % mandelic acid
d. a glycol;
e. a salt-tolerant thickening polymer and/or dispersing polymer,
wherein the total amount of glycolic acid, gluconolactone and mandelic acid is less than about 15 wt. % of the total composition.

In another aspect, the invention pertains to a composition for the treatment of acne comprising:
a. about 2.5 wt. % to about 7.5 wt. % glycolic acid;
b. about 1 wt. % to about 5 wt. % gluconolactone;
c. about 1 wt. % to about 5 wt. % mandelic acid
d. about 2.5 wt. % to about 7.5 wt. % propylene glycol;
e. about 0.5 wt. % to about 2 wt. % polyacrylate crosspolymer-6; and
f. about 0.5 wt. % to about 2 wt. % hydroxyethyl acrylate/sodium acryloyldimethyl taurate copolymer,
wherein the total amount of glycolic acid, gluconolactone and mandelic acid is less than about 12 wt. % of the total composition.

Other Additives

A variety of other materials may also be present in the compositions used in accordance with principles of the present invention of the present invention. In certain embodiments, the composition comprises one or more topical ingredients selected from the group consisting of: surfactants, chelating agents, emollients, humectants, conditioners, preservatives, opacifiers, fragrances and the like.

What is meant by an emollient is a compound that helps to maintain the soft, smooth, and pliable appearance of the skin (e.g., by remaining on the skin surface or in the stratum corneum to act as a lubricant). Examples of suitable emollients include those found in Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.), and include, but are not limited to, petrolatum, hexyldecyl stearate, dimethicone, neopentyl glycol diheptanoate, and plant, nut, and vegetable oils such as macadamia nut oil, rice bran oil, grape seed oil, palm oil, prim rose oil, hydrogenates peanut oil, and avocado oil.

What is meant by a humectant is a compound intended to increase the water content of the top layers of skin (e.g., hygroscopic compounds). Examples of suitable humectants include those found Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.) and include, but are not limited to, glycerin, sorbitol or trehalose (e.g., $\alpha,\alpha$-trehalose, $\beta,\beta$-trehalose, $\alpha,\beta$-trehalose) or a salt or ester thereof (e.g., trehalose 6-phosphate).

What is meant by a surfactant is a surface-active agent intended to cleanse or emulsify. Examples of suitable surfactants include those found in Chapter 37, pages 431-450 (Classification of surfactants, by L. Oldenhove de Guertechin) in Handbook of Cosmetic Science and Technology (edited by A. Barel, M. Paye and H. Maibach, Published in 2001 by Marcel Dekker, Inc., New York, N.Y.) and include, but are not limited to anionic surfactants such as sulfates, cationic surfactants such as betaines, amphoteric surfactants such as sodium coco glycinate, nonionic surfactants such as alkyl polyglucosides.

Examples of suitable chelating agents include those which are capable of protecting and preserving the compositions of this invention. In certain embodiments, the chelating agent is ethylenediamine tetracetic acid ("EDTA"), and in further embodiments is tetrasodium EDTA, available commercially from Dow Chemical Company of Midland, Michigan under the trade name, "Versene 100XL."

Suitable preservatives include, for example, parabens, quaternary ammonium species, phenoxyethanol, benzoates, DMDM hydantoin, organic acids, phenoxyethanol and are present in the composition in an amount, based upon the total weight of the composition, from about 0 to about 1 percent or from about 0.05 percent to about 0.5 percent.

Any of a variety of commercially available pearlescent or opacifying agents are suitable for use in the composition. Examples of suitable pearlescent or opacifying agents include, but are not limited to, mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: HO-(JO)a-H, wherein J is an alkylene group having from about 2 to about 3 carbon atoms; and a is 2 or 3; fatty alcohols containing from about 16 to about 22 carbon atoms; fatty esters of the formula: $KCOOCH_2L$, wherein K and L independently contain from about 15 to about 21 carbon atoms; inorganic solids insoluble in the shampoo composition, and mixtures thereof.

Any fragrance compositions suitable for use on skin may be used in accord with the present invention.

Any suitable carrier may be used in the compositions. Particularly, the carrier is a cosmetically acceptable carrier. As will be recognized by those of skill in the art, cosmetically acceptable carriers comprise carriers that are suitable for use in contact with the body, in particular the skin, without undue toxicity, incompatibility, instability, irritation, allergic response, and the like. A safe and effective amount of carrier is from about 50% to about 99.999%, particularly from about 80% to about 99.9%, more particularly from about 99.9% to about 95%, most particularly from about 98% to about 99.8% of the composition.

The following are non-limitative examples of carriers. Other carriers can be formulated by those of ordinary skill in the art. In one embodiment, the carrier contains water. In a further embodiment, the carrier may also contain one or more aqueous or organic solvents. Examples of organic solvents include, but are not limited to, dimethyl isosorbide; isopropyl myristate; surfactants of cationic, anionic and nonionic nature; vegetable oils; mineral oils; waxes; gums; synthetic and natural gelling agents; alkanols; and polyols.

Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about 15 carbon atoms (e.g., from about 2 carbon atoms to about 10 carbon atoms) such as propylene glycol. The organic solvents may be present in the carrier in an amount, based upon the total weight of the carrier, of from about 1 percent to about 99.99 percent (e.g., from about 20 percent to about 50 percent). Water may be present in the carrier (prior to use) in an amount, based upon the total weight of the carrier, of from about 5 percent to about 95 percent (e.g., from about 50 percent to about 90 percent). Solutions may contain any suitable amounts of solvent, including from about 40 to about 99.99%. Certain preferred solutions contain from about 50 to about 99.9%, from about 60 to about 99%, from about 70 to about 99%, from about 80 to about 99%, or from about 90 to 99% of solvent.

The compositions used in accordance with principles of the present invention may further comprise any of a variety of additional cosmetically active agents. Examples of suitable additional active agents include: skin lightening agents, darkening agents, additional anti-aging agents, tropoelastin promoters, collagen promoters, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, odor-control agents such as odor masking or pH changing agents, and the like.

Examples of various suitable additional cosmetically acceptable actives include benzoyl peroxide; D-panthenol; UV filters such as but not limited to avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate 0 (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octrocrylene, oxybenzone (Eusolex 4360), sulisobenzone, bisoctrizole (Tinosorb M), titanium dioxide, zinc oxide; carotenoids; free radical scavengers; spin traps; retinoids and retinoid precursors such as 30 retinol, retinoic acid and retinyl palmitate; ceramides; polyunsaturated fatty acids; essential fatty acids; enzymes; enzyme inhibitors; minerals; hormones such as estrogens; steroids such as hydrocortisone; 2-dimethylaminoethanol; copper salts such as copper chloride; peptides containing copper such as Cu:Gly-His-Lys, coenzyme Q10; amino acids such a proline; vitamins; lactobionic acid; acetyl-coenzyme A; niacin; riboflavin; thiamin; ribose; electron transporters such as NADH and FADH2; and other botanical extracts such as oat, aloe vera, Feverfew, Soy, Shiitake mushroom extracts, and derivatives and mixtures thereof.

Product Form and Packaging

The composition can be made into a wide variety of product forms. For example, compositions in the form of emulsions, including, but not limited to, oil-in-water, water-in-oil, water-in-oil-in-water, and oil-in-water-in-silicone emulsions, are useful herein. These emulsions can cover a broad range of viscosities, e.g., from about 100 cps to about 200,000 cps. Reference in the instant application is made to two types of viscosity measurements: A) "rheometer viscosity," which is measured as a steady-state value at an applied shear rate of 20 $s^{-1}$ in a rheometer, at 25° C., and B) "Brookfield viscosity," which is measured at 5 or 10 RPM after one minute at 25° C. in 4 oz jar using spindle RV #4 or RV #5. Unless otherwise specified, the viscosity referenced is the rheometer viscosity.

Examples of suitable forms include solutions, suspensions, lotions, creams, serums, essences, gels, toners, sticks, sprays, ointments, liquid washes and soap bars, shampoos, hair conditioners, pastes, foams, mousses, powders, shaving creams, wipes, patches, strips, powered patches, microneedle patches, bandages, hydrogels, film-forming products, facial and skin masks, make-up, liquid drops, and the like.

In one or more embodiments, the compositions described herein are in the form of a serum or lotion. As used herein, the term "serum" or "lotion" means a predominantly water-containing topical preparation of light texture and fresh watery sensation, having a viscosity of from about 1,000 cPs to 4,000 cPs. Lotions or serums typically contain at least one emollient in addition to a solvent. Lotions/serums may comprise from about 1% to about 20% (e.g., from about 5% to about 10%) of an emollient(s) and from about 50% to about 90% (e.g., from about 60% to about 80%) of water.

In some embodiments, the compositions described herein are in the form of a cream. As used herein, the term "cream" means a predominantly water-containing topical preparation of rich texture having a viscosity of from about 2,000 cPs to 8,000 cPs. A cream typically contains from about 5% to about 50% (e.g., from about 10% to about 20%) of an emollient(s) and from about 45% to about 85% (e.g., from about 50% to about 75%) of water.

In one or more embodiments, the compositions described herein are in the form of an ointment. As used herein, the term "ointment" means a predominantly oil-containing topical preparation of thick texture having a viscosity of from about 10,000 cPs to about 40,000 cPs. An ointment may contain a simple base of animal, vegetable, or synthetic oils or semi-solid 10 hydrocarbons. An ointment may contain from about 2% to about 10% of an emollient(s) plus from about 0.1% to about 2% of a thickening agent(s).

The compositions useful in the present invention can also be formulated as emulsions. If the carrier is an emulsion, from about 1% to about 10% (e.g., from about 2% to about 5%) of the carrier contains an emulsifier(s). Emulsifiers may be nonionic, anionic or cationic.

Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type, and water-in-oil type are well-known in the art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel. As used herein, the term "gel" means a predominantly water-containing topical preparation of rich texture containing dispersing polymer and exhibiting yield value of about 0.1 Pa or more. The gel may contain a gelling agent. Such gels typically contain between about 0.1% and 5%, by weight, of such gelling agents.

The compositions of the present invention can also be formulated into a solid formulation (e.g., a wax-based stick, soap bar composition, powder, or wipe). The composition of the present invention can also be combined with a solid, semi-solid, or dissolvable substrate (e.g., a wipe, mask, pad, glove, or strip).

The compositions described herein can be provided to the consumer in a container, e.g., a bottle, tube, etc. Individual packets enclosing measured portions of the composition may also be used.

To dispense the composition from a bottle, a pump, squeezable valve, or a removable screw cap may be used.

EXAMPLES

Examples 1A-C: Compositions and Properties

Several compositions were prepared and evaluated as shown below. The viscosity values shown in the results of the Examples section are Brookfield viscosities, and were measured with a Brookfield viscometer DV-II+ PRO. For E1-3 RVT spindle #4 at 5 rpm was used with a value read after 1 minute. For E4-E22, an RVT spindle #5 at 5 rpm was used and a value was taken after 1 minute. All the measurements were done in a 4 oz glass jar at 22° C.

E1-3 were prepared according to the following protocol: Premix A: Add 10% water, propylene glycol, glycolic acid, gluconolactone, mandelic acid, and salicylic acid (if included). Mix for a minimum of 1.5 hours. Adjust the pH of this premix to 3.8 using 20% Sodium Hydroxide solution. Main Phase: Add water, chelating agent, Hydroxyethyl Acrylate/Sodium Acryloyldimethyl Taurate Copolymer, Polyacrylate Crosspolymer-6. Begin the homogenizer, add miscellaneous ingredients. Homogenize until formula is uniform, free of undissolved particles, and a proper emulsion is formed.

Compositions E4-E17 were prepared according to the following protocol: Acid Premix: Add 10% water, propylene glycol, glycolic acid, gluconolactone, mandelic acid and Salicylic Acid (if included). Mix for a minimum of 1.5 hours. Adjust the pH of this premix to 3.5-3.8 using 20% Sodium Hydroxide solution. Main Phase: Add water, Polymer(s) (Hydroxyethyl Acrylate/Sodium Acryloyldimethyl Taurate Copolymer and Polyacrylate Crosspolymer-6, or Ammonium Acryloyldimethyltaurate/Carboxyethyl Acrylate Crosspolymer or Sodium Acryloyldimethyltaurate/VP Crosspolymer or Hydroxyethylcellulose). For E15 where Hydroxyethylcellulose was used 1,3-Butelene Glycol was added to the main phase and the main phase was heated to 75° C. until polymer was fully dissolved. Homogenize until formula is uniform, free of undissolved particles homogenizer; add acid(s) premix and mix for 15 mins; add miscellaneous ingredients. Homogenize until formula is uniform, free of undissolved particles, and a proper emulsion is formed. Adjust pH to be between 3.4 to 4.0 using 20% sodium hydroxide solution. For E1-3, the formula is pH adjusted to be 3.8.

| INCI | E1 | E2 | E3 | E4 | E5 | E6 | E7 | E8 | E9 | E10 | E11 | E12 |
|---|---|---|---|---|---|---|---|---|---|---|---|---|
| Propylene glycol | 5 | 5 | 5 | 5 | 5 | 5 | 5 | 5 | 5 | 5 | 5 | 5 |
| Glycolic Acid (70% active in water) | 7.14 | 7.14 | 7.14 | 4 | 4 | 2.86 | 2.86 | 7.14 | 7.14 | 7.14 | 7.14 | 7.14 |
| Gluconolactone | 2.45 | 2.45 | 2.45 | 3 | 3 | 5 | 5 | 2.45 | 2.45 | 2.45 | 2.45 | 2.45 |
| Mandelic Acid | 2.55 | 2.55 | 2.55 | 3 | 3 | 3 | 3 | 2.55 | 2.55 | 2.55 | 2.55 | 2.55 |
| Salicylic Acid | 0.5 | — | 0.5 | — | — | — | — | — | 0.5 | 0.5 | — | 0.5 |
| Sodium Hydroxide | QS | QS | QS | QS | QS | QS | QS | QS | QS | QS | QS | QS |
| Water | QS | QS | QS | QS | QS | QS | QS | QS | QS | QS | QS | QS |
| Polyacrylate Crosspolymer-6[1] | 1.3 | 1.3 | 1.0 | 0.5 | 1 | 1 | 1.5 | 1.5 | 1.5 | 1.5 | 1.5 | 1.3 |
| Hydroxyethyl Acrylate/Sodium Acryloyldimethyl Taurate Copolymer[2] | 1.4 | 1.4 | 1.4 | 0.5 | 1 | 1 | 1.5 | 1.5 | 1.5 | 1.5 | 1.5 | 1.4 |
| Dimethicone and Dimethicone Crosspolymer[3] | 4.5 | 4.5 | 4.5 | — | — | — | — | 4.5 | 4.5 | — | 4.5 | 4.5 |
| Misc. (e.g., Fragrance, Chelating Agents, Emollients, Surfactants, Preservatives, Film Forming Agents) | 2.25 | 2.25 | 2.2 | 1.65 | 1.65 | — | — | 2.1 | 2.3 | 5.1 | 2.25 | 2.25 |
| Total acid | 10.5 | 10.5 | 10.5 | 8.8 | 8.8 | 10.0 | 10.0 | 10.0 | 10.5 | 10.5 | 10.0 | 10.5 |
| Brookfield Viscosity | 18440 | 20400 | 9840 | 900 | 3,100 | 3,300 | 16,760 | 13,920 | 13,610 | | 21,360 | 11,320 |
| pH | 3.80 | 3.80 | 3.80 | | | 3.69 | 3.69 | | 3.6 | 3.5 | 3.62 | 3.51 |

[1] Sepimax Zen™
[2] Sepinov™ EMT 10
[3] Blend of Xiameter™ PMX-200 Silicone Fluid, Dow Corning® Q7-9120 Silicone Fluid and Dowsil™ 9041 Silicone Elastomer Blend As can be seen from the above table, Compositions E1-12 containing a total amount of acids of about or below 10.5 weight percent of AHA, PHA and (optionally) BHA; in combination of varying levels of salt-tolerant thickening polymers yielded formulations of different forms, lotion or serums (E1-E3), lotions (E4-E6), creams (E5, E6) or ointments (E7-12). All viscosities were measure by method set forth above.

Example 1B: Effect of Polymer Type on Viscosity

Five compositions were created according to the table below and measured for viscosity.

| INCI | E13 | E14 | E15 | E16 | E17 |
|---|---|---|---|---|---|
| 1,3-Butelene Glycol | — | — | 3 | — | — |
| Propylene Glycol | 5 | 5 | — | 5 | 5 |
| Glycolic Acid (70% active in water) | 2.86 | 2.86 | 4 | 7.14 | 7.14 |
| Gluconolactone | 5 | 5 | 3 | 2.5 | 2.5 |
| Mandelic Acid | 3 | 3 | 3 | 2.5 | 2.5 |
| Sodium Hydroxide | QS | QS | QS | QS | QS |
| Water | QS | QS | QS | QS | QS |
| Polyacrylate Crosspolymer-6[1] | 1 | 1.5 | — | — | — |
| Hydroxyethyl Acrylate/Sodium Acryloyldimethyl Taurate Copolymer[2] | 1 | 1.5 | — | — | — |
| Ammonium Acryloyldimethyltaurate/Carboxyethyl Acrylate Crosspolymer[3] | — | — | — | 2.5 | — |
| Sodium Acryloyldimethyltaurate/VP Crosspolymer[4] | — | — | — | — | 2.5 |
| Hydroxyethylcellulose | — | — | 0.75 | — | — |
| Total acid | 10.0 | 10.0 | 8.8 | 10.0 | 10.0 |
| Brookfield Viscosity | 3,300 | 16,760 | 8,000 | 3,000 | 12,500 |
| pH | 3.69 | 3.69 | 3.51 | 3.65 | 3.68 |

[1]Sepimax Zen ™
[2]Sepinov ™ EMT 10
[3]Aristoflex ® AVC
[4]Aristoflex ® AVS

As can be seen from the above table, polymers of different nature were used to build up viscosity depending on the forms of the product desired. Compositions containing acrylate-based crosspolymers such as acryloyldimethyltaurate/VP copolymer (E16, E17), combination of polyacrylate crosspolymer-6 and hydroxyethyl acrylate/sodium acryloyldimethyl taurate copolymer (E13 and E14) and cellulose-based polymers such as hydroxyethylcellulose (E15) were made and viscosities were measured. Further, compositions formulated with sodium acryloyldimethyltaurate/VP crosspolymer (E16) exhibited a higher viscosity than composition formulated with ammonium acryloyldimethyltaurate/carboxyethyl acrylate at the same polymer concentration, thus making sodium acryloyldimethyltaurate/VP crosspolymer a more viscosity-enhancing agent.

Example 1C: Effect of Acid Addition on Viscosity

Five samples were prepared according to the table below.

| | E18 (Comp) | E19 (Comp) | E20 (Comp) | E21 (Comp) | E22 (Inv) |
|---|---|---|---|---|---|
| Propylene glycol | — | 5 | 5 | 5 | 5 |
| Glycolic Acid (70% active in water) | — | 3 | — | — | 2 |
| Gluconolactone | — | — | 3 | — | 5 |
| Mandelic Acid | — | — | — | 3 | 3 |
| Sodium Hydroxide | QS to 3.5 | QS to 3.5 | QS to 3.5 | QS to 3.5 | QS to 3.5 |
| Polyacrylate Crosspolymer-6[1] | 1 | 1 | 1 | 1 | 1 |
| Hydroxyethyl Acrylate/Sodium Acryloyldimethyl Taurate Copolymer[2] | 1 | 1 | 1 | 1 | 1 |
| Water | QS to 100 | QS to 100 | QS to 100 | QS to 100 | QS to 100 |
| final Brookfield viscosity | 54,000 | 6,800 | 14,400 | 10,000 | 3,300 |
| final pH | 3.64 | 3.40 | 3.61 | 3.56 | 3.62 |

[1]Sepimax Zen ™
[2]Sepinov ™ EMT 10

E18-22 were prepared according to the following protocol: Acid Premix: Add 10% water, propylene glycol, glycolic acid and/or gluconolactone and/or mandelic acid. Mix for a minimum of 1.5 hours. Adjust the pH of this premix to 3.5-3.8 using 20% Sodium Hydroxide solution. Main Phase: Add water, Hydroxyethyl Acrylate/Sodium Acryloyldimethyl Taurate Copolymer, Polyacrylate Crosspolymer-6. Homogenize until formula is uniform, free of undissolved particles homogenizer; add acid(s) premix and mix for 15 mins, adjust pH to be between 3.4 to 4.0 using 20% sodium hydroxide solution.

As can be seen from the above table, when acid is added, the viscosity decreases compared to the formula without acid (E18). The addition of glycolic acid in E19 exhibited the greatest drop in viscosity compared to gluconolactone in E20 or mandelic acid in E21. At the same acid concentration, compositions containing glycolic acid required the highest amount of Sodium hydroxide to adjust pH to desired values as compared to gluconolactone and/or Mandelic acid. Therefore, the example with glycolic acid (E19) contains the highest amount of salt which results in the strongest effect on polymer in reducing viscosity. Combining gluconolactone and mandelic acids in E22 exhibited an additive effect and an even more profound drop in viscosity thus would require more polymer to effectively build up viscosity.

Example 1D: Effect of Polymer Selection on Stability

Thirteen samples (six comparative and seven inventive) were prepared having the ingredients shown in the tables below, and then evaluated for stability, rheometer viscosity and yield. Stability was determined by the presence of separation after one month at 50° C.

The samples were prepared according to the following protocol: Premix A: Add 10% water, propylene glycol, glycolic acid, gluconolactone, mandelic acid, and salicylic acid. Mix for a minimum of 1.5 hours. Adjust the pH of this premix to 3.8 using 20% Sodium Hydroxide solution. Main Phase: Add water, chelating agent, polymer(s), mix until uniform (heat up to 80° C. if necessary). Begin the homogenizer, add miscellaneous ingredients. Homogenize until formula is uniform, free of undissolved particles, and a proper emulsion is formed. Adjust pH to be between 3.6 to 4.0 using 20% sodium hydroxide solution. All formulations have a salt content above 2%.

Comparative Formulations

|  | E23 (Comp.) | E24 (Comp.) | E25 (Comp.) | E26 (Comp.) | E27 (Comp.) | E28 (Comp.) |
| --- | --- | --- | --- | --- | --- | --- |
| Propylene glycol | 5 | 5 | 5 | 5 | 5 | 5 |
| Glycolic Acid (70% active in water) | 7.14 | 7.14 | 7.14 | 7.14 | 7.14 | 7.14 |
| Gluconolactone | 2.45 | 2.45 | 2.45 | 2.45 | 2.45 | 2.45 |
| Mandelic Acid | 2.55 | 2.55 | 2.55 | 2.55 | 2.55 | 2.55 |
| Sodium Hydroxide | QS | QS | QS | QS | QS | QS |
| Water | QS | QS | QS | QS | QS | QS |
| Acrylates Copolymer (30% active)[1] | 10 | | | | | |
| Acrylates Crosspolymer-4 (30% active)[2] | | 10 | | | | |
| Acrylates/C10-30 Alkyl Acrylate Crosspolymer[3] | | | 3 | 4 | | |
| Carbomer[4] | | | | | 3 | |
| Polyurethane-62 (and) Trideceth-6[5] | | | | | | 2 |
| Chelating agent | 0.1 | 0.1 | 0.1 | 0.1 | 0.1 | 0.1 |
| Dimethicone; Dimethicone Crosspolymer[6] | — | — | 4.5 | 4.5 | 4.5 | 4.5 |
| Misc. (Emollient and preservative) | — | — | 3 | 3 | 3 | 3 |
| Total acid | 10 | 10 | 10 | 10 | 10 | 10 |
| Stability | unstable | unstable | unstable | unstable | unstable | unstable |
| Rheometer Viscosity, Pa*s | — | — | 3.352 | 4.989 | 0.028 | 2.360 |
| Yield Value, Pa | — | — | 1.67 | 3.04 | 0.00 | 0.00 |

[1]Carbopol ® Aqua SF-1
[2]Carbopol ® Aqua SF-2
[3]Carbopol ® Ultrez 20
[4]Carbopol ® Ultrez 10
[5]Avalure ™ Flex-6
[6]Blend of Xiameter ™ PMX-200 Silicone Fluid, Dow Corning ® Q7-9120 Silicone Fluid and Dowsil ™ 9041 Silicone Elastomer Blend Comparative Polymer Descriptions

| Tradename | INCI | Description |
|---|---|---|
| Carbopol® Ultrez 10 Polymer | Carbomer | Carbomer is a homopolymer of Acrylic Acid (q.v.) crosslinked with an allyl ether of Pentaerythritol (q.v.), an allyl ether of Sucrose (q.v.), or an allyl ether of propylene. |
| Carbopol® Ultrez 20 Polymer | Acrylates/C10-30 Alkyl Acrylate Crosspolymer | Acrylates/C10-30 Alkyl Acrylate Crosspolymer is a copolymer of C10-30 Alkyl Acrylate (q.v.) and one or more monomers of Acrylic Acid (q.v.), Methacrylic Acid (q.v.) or one of their simple esters crosslinked with an allyl ether of Sucrose (q.v.) or an allyl ether of Pentaerythritol (q.v.). |
| Carbopol® Aqua SF-1 Polymer | Acrylates Copolymer | Acrylates Copolymer is a copolymer of two or more monomers consisting of Acrylic Acid (q.v.), Methacrylic Acid (q.v.) or one of their simple esters. |
| Carbopol® Aqua SF-2 Polymer | Acrylates Crosspolymer-4 | Acrylates Crosspolymer-4 is a copolymer of Acrylic Acid (q.v.), Methacrylic Acid (q.v.) or one of its simple esters, crosslinked with Trimethylolpropane Triacrylate (q.v.) |

Inventive Formulations

|  | E29 (Inv.) | E30 (Inv.) | E31 (Inv.) | E31 (Inv.) | E32 (Inv.) | E33 (Inv.) | E34 (Inv.) |
|---|---|---|---|---|---|---|---|
| Propylene glycol | 5 | 5 | 5 | 5 | 5 | 5 | 5 |
| Glycolic Acid (70% active) | 7.14 | 7.14 | 7.14 | 7.14 | 7.14 | 7.14 | 7.14 |
| Gluconolactone | 2.45 | 2.45 | 2.45 | 2.45 | 2.45 | 2.45 | 2.45 |
| Mandelic Acid | 2.55 | 2.55 | 2.55 | 2.55 | 2.55 | 2.55 | 2.55 |
| Sodium Hydroxide | QS | QS | QS | QS | QS | QS | QS |
| Water | QS | QS | QS | QS | QS | QS | QS |
| Polyacrylate Crosspolymer-6[1] | 1.4 | 2.7 |  |  |  |  |  |
| Hydroxyethyl Acrylate/Sodium Acryloyldimethyl Taurate Copolymer[2] | 1.3 |  | 2.7 |  |  |  |  |
| Sodium Polyacryloyl-dimethyl Taurate[3] |  |  |  | 3 |  |  |  |
| Ammonium Acryloyl-dimethyltaurate/Beheneth-25 Methacrylate Crosspolymer[4] |  |  |  |  | 3 |  |  |
| Xanthan Gum[5] |  |  |  |  |  | 2 |  |
| Hydroxypropyl Methylcellulose[6] |  |  |  |  |  |  | 1 |
| Chelating agent | 0.1 | 0.1 | 0.1 | 0.1 | 0.1 | 0.1 | 0.1 |
| Dimethicone and Dimethicone Crosspolymer[7] | 4.5 | 4.5 | 4.5 | 4.5 | 4.5 | 4.5 | 4.5 |
| Misc. (Emollient and preservative) | 3 | 3 | 3 | 3 | 3 | 3 | 3 |
| Total acid | 10 | 10 | 10 | 10 | 10 | 10 | 10 |
| Stability | stable | stable | stable | stable | stable | stable | stable |
| Rheometer Viscosity, Pa*s | 12.700 | 57.713 | 1.369 | 92.471 | 7.204 | 79.724 | 36.475 |
| Yield Value, Pa | 11.45 | 89.37 | 0.73 | 125.44 | 6.83 | 74.84 | 0.00 |

[1] Sepimax Zen ™
[2] Sepinov ™ EMT 10
[3] Aristoflex® Silk
[4] Aristoflex® HMB
[5] Rheocare XGN
[6] Benecel K200M
[7] Blend of Xiameter™ PMX-200 Silicone Fluid, Dow Corning® Q7-9120 Silicone Fluid and Dowsil™ 9041 Silicone Elastomer Blend Inventive Polymer Descriptions

| Tradename | INCI | Description |
|---|---|---|
| Aristoflex ® HMB | Ammonium Acryloyldimethyltaurate/ Beheneth-25 Methacrylate Crosspolymer | Ammonium Acryloyldimethyltaurate/Beheneth-25 Methacrylate Crosspolymer is a copolymer of Ammonium AMPS (q.v.) and Beheneth-25 Methacrylate (q.v.) monomers |
| Aristoflex ® Silk | Sodium Polyacryloyldimethyl Taurate | Sodium Polyacryloyldimethyl Taurate is an anionic polymer from acrylamide alkyl sulfonic acid or salt thereof. |
| Sepinov ™ EMT 10 | Hydroxyethyl Acrylate/Sodium Acryloyldimethyl Taurate Copolymer | Hydroxyethyl Acrylate/Sodium Acryloyldimethyl Taurate Copolymer is a copolymer of sodium hydroxyethyl acrylate and acryloyldimethyl taurate monomers. |
| Sepimax Zen ™ | Polyacrylate Crosspolymer-6 | Polyacrylate Crosspolymer-6 is a copolymer of Ammonium AMPS (q.v.), Dimethylacrylamide (q.v.), Lauryl Methacrylate (q.v.) and laureth-4 methacrylate, crosslinked with Trimethylolpropane Triacrylate (q.v.) |
| Rheocare ® XGN | Xanthan Gum | Polysaccharide consisting of glucose, mannose and glucuronic acid |
| Benecel ™ K200M | Hydroxypropyl Methylcellulose | Hydroxypropyl Methylcellulose is a propylene glycol ether of Methylcellulose |

As can be seen from the above tables, comparative compositions E23-28 were all unstable, while inventive compositions E29-34 were all stable. As here in, stable means that samples passed accelerated stability study at 50 C for 1 month and showed no visual changes such as phase-separation; and did not show significant changes in pH and viscosity. As the compositions were all similar except for variation in the selection of polymers, the above data are informative regarding the polymers which can be used to result in a stable formula. The inventive formulations all feature the use of salt-tolerant polymers, and particularly either sulfonate-containing moieties or cellulose-based moieties, while the comparative formulations do not.

As can be seen from the above table, compositions E29-34 containing varying levels of salt-tolerant thickening polymers yielded formulations of different forms, lotions or serums (E31), creams (E32) or ointments (E29, E30, E33, E34). All viscosities were measure by method set forth above.

As can be seen from the above table, the compositions E29-E33 are in the form of a gel as they contain dispersing polymer and exhibit yield value of about 0.1 Pa or more.

Examples 2A-D: Clinical Study

A 12-week, single-center, evaluator blind, randomized controlled clinical trial was performed to evaluate the efficacy and tolerance of inventive compositions (E1 and E2) in improving acne and the complexion of acne subjects with mild to moderate acne vulgaris. The breakdown of ingredients of the compositions are reproduced in the table below. E1 and 2 are the same except E1 contains salicylic acid, while E2 contains water in place of the salicylic acid. 35 subjects completed treatment with E1, and 32 subjects completed treatment with E2.

Compositions Used in Clinical Experiments

| INCI | E1 (Inv.) | E2 (Inv.) |
|---|---|---|
| Water | 70.51 | 71.01 |
| Sodium Hydroxide | 2.4 | 2.4 |
| Propylene Glycol | 5 | 5 |
| Glycolic Acid (70% active in water) | 7.14 | 7.14 |
| Gluconolactone | 2.45 | 2.45 |
| Mandelic Acid | 2.55 | 2.55 |
| Salicylic Acid | 0.5 | — |
| Hydroxyethyl Acrylate/Sodium Acryloyldimethyl Taurate Copolymer[1] | 1.4 | 1.4 |
| Polyacrylate Crosspolymer-6[2] | 1.3 | 1.3 |
| Dimethicone (and) Dimethicone Crosspolymer[3] | 4.5 | 4.5 |
| Misc. (Fragrance, chelating agent, skin conditioning agent etc.) | 2.25 | 2.25 |

[1]Sepinov ™ EMT 10
[2]Sepimax Zen ™
[3]Blend of Xiameter ™ PMX-200 Silicone Fluid, Dow Corning ® Q7-9120 Silicone Fluid and Dowsil ™ 9041 Silicone Elastomer Blend Subjects used their assigned treatment once per day (evening) for the first week followed by twice per day (morning and evening) for the remainder of the study. The study Investigator assessed for acne lesion counts, global acne assessment, and additional clinical graded efficacy. Tolerance was evaluated by the Investigator, as well as through self-assessments. The Table below shows the results. Data indicates the total % of subjects who showed improvement, in at least one sub-attribute of the larger benefit bucket, between both treatments, in the various attributes.

| Investigator Grading - % of Subjects Showing Improvement vs. baseline at week 12 | E2 (Formula without Sal Acid) | E1 (Formula with Sal Acid) |
|---|---|---|
| Acne (Acne Lesion Count or Investigator Global Acne Assessment) | 90.6% | 93.5% |
| Marks (Size, Color or Severity) | 81.3% | 51.6% |
| Tone (Skin Clarity, Blotchiness, or Overall Uneven Skin Tone) | 90.6% | 80.6% |
| Texture (Tactile Surface Roughness) | 90.6% | 93.5% |
| Inflammatory Lesions (Size or Redness) | 81.3% | 80.6% |
| Tolerance - % of subjects demonstrating scores of "none to mild" at week 12 | 93.7% | 96.8% |
| Erythema | 100% | 100% |
| Edema | 100% | 100% |
| Dryness/Scaling | 100% | 100% |
| Burning/Stinging | 100% | 100% |
| Itching | 100% | 100% |
| Tightness | 100% | 100% |

As can be seen from the results, the treatments provided statistically and clinically meaningful reductions in total lesion counts (inflammatory and non-inflammatory) as per Investigator grading over the 12-week clinical study, starting at week 2, with no statistically significant difference in total lesion count between treatment A and B at the 12-week time point. In addition, both treatments improved the redness of inflammatory lesions, the skin's surface roughness and overall skin blotchiness, with no statistically significant differences in grading at the 12-week time point. Both products were found to be well-tolerated, with no statistically significant increase in any of the tolerance attributes assessed. The degree to which the products were well-tolerated was also surprising, given the relatively high acid content of the products.

Examples 3A-C: Microbiology Study

Two inventive compositions were tested against two placebo compositions and evaluated for their effect on *Cutibacterium acnes* (*C. acnes*), both in planktonic and biofilm states. The two inventive compositions are the same E1 and 2 from above. E1 and 2 are the same except E1 contains salicylic acid, while E2 contains water in place of the salicylic acid. The two placebo compositions correspond to E1 and 2, except the placebo compositions do not contain propylene glycol, or any acids. Placebo 1 has a pH of 4.5, which corresponds to the resulting pH when said ingredients are removed without additional pH adjustment. Placebo 2 has been pH adjusted to 3.8, which is the pH of E1 and 2 to account for any pH effect. The breakdown of ingredients of the compositions are shown in the table below.

Compositions Used in Microbiology Experiments

| INCI | E1 (Inv.) | E2 (Inv.) | Placebo 1, pH 4.5 (Comp.) | Placebo 2, pH 3.8 (Comp.) |
|---|---|---|---|---|
| Water | 70.51 | 71.01 | 91 | 91 |
| Sodium Hydroxide | QS to pH 3.8 | QS to pH 3.8 | | |
| Propylene Glycol | 5 | 5 | | |
| Glycolic Acid (70% active in water) | 7.14 | 7.14 | | |
| Gluconolactone | 2.45 | 2.45 | | |
| Mandelic Acid | 2.55 | 2.55 | | |
| Salicylic Acid | 0.5 | — | | |
| Hydroxyethyl Acrylate/Sodium Acryloyldimethyl Taurate Copolymer[1] | 1.4 | 1.4 | 1.4 | 1.4 |
| Polyacrylate Crosspolymer-6[2] | 1.3 | 1.3 | 1.0 | 1.0 |
| Dimethicone (and) Dimethicone Crosspolymer[3] | 4.5 | 4.5 | 4.5 | 4.5 |
| Misc. (Fragrance, chelating agent, skin conditioning agent etc.) | 2.25 | 2.25 | 2.1 | 2.1 |
| Citric Acid | | | | Q.S. to 0.06 as needed |

[1]Sepinov™ EMT 10
[2]Sepimax Zen™
[3]Blend of Xiameter™ PMX-200 Silicone Fluid, Dow Corning® Q7-9120 Silicone Fluid and Dowsil™ 9041 Silicone Elastomer Blend Placebo 1 was prepared by adding water, chelating agent, hydroxyethyl acrylate/sodium acryloyldimethyl taurate copolymer, and polyacrylate crosspolymer-6. The mixture was then homogenized in a homogenizer, followed by addition of the miscellaneous ingredients. The mixture was homogenized until the formula was uniform, free of undissolved particles, and a proper emulsion formed. Placebo 2 was prepared in the same manner as Placebo 1, except the pH was adjusted to 3.8 using citric acid solution.

Example 3A: Effect on Planktonic Bacteria

Planktonic bacteria were treated with E1-2 and Placebos 1-2 and evaluated for effect. The protocols used are described below.
Assay: *C. acnes* Microbial Kill Time Assay (Standard Planktonic Test Method)
Test Organism: *Cutibacterium acnes* (*C. acnes*) ATCC 11827
Laboratory Procedure:
Organism Preparation: Prepare organism inocula by making a direct suspension of isolated colonies in sterile saline from an agar plate. a. Using a spectrophotometer, target approximately Target 1.0 OD600 on spectrophotometer for approximate 108-109 CFU/mL suspension. Further dilute in saline to 107 CFU/mL and 105 CFU/mL.
1:50 Neutralizer Validation: Weigh 0.2 grams of test sample and dilute 1:50 in 9.8 mL of neutralizer. b. Make a control tube containing 9.8 mL neutralizer and 0.2 mL saline. Add 100 µL of inoculum (105 CFU/mL of standardized inoculum above) to all neutralization tubes and control tubes to yield 10-100 CFU/mL. After 10 minutes, aliquot 0.1 mL and spread plate onto RCA, in duplicate. Incubate anaerobically at 35±2.5° C. for 5-7 days. Count colonies and calculate the average CFU/mL. Recovery of less than 50% CFU/mL neutralizer versus CFU/mL of the inoculum control indicates toxicity.
Microbial Kill Time Study
Weigh 5 grams of each test sample in a sterile sample cup. Inoculate each sample cup with 50 µL of inoculum (107 CFU/mL). Start timer and mix thoroughly; sample at 10 minutes. After time is up, transfer 0.2 grams of inoculated test sample into 9.8 mL of neutralizer. Run a blank sample of saline in the same manner.

Dilutions and Plating: After the initial 1:50 dilution, carry out additional 1:50 dilutions in saline. Aliquot 0.1 mL from the initial 1:50 dilution and spread plate onto RCA, in duplicate. All plates after the initial 1:50 dilution will be generated as spot plates: Divide agar plate into quadrants with marker on the bottom of the plate. Prepare duplicate plates per each sample. Each plate receives up to 5 dilutions of one sample. Use a multi-dispense pipettor to draw up 100 µL of sample: Dispense 5 spots of 10 µL each into one quadrant of the plate. Dispense the next 5 spots of 10 µL onto one quadrant of the duplicate plate. Continue for each dilution needed per sample.

After fluid is absorbed, invert plates and incubate in anaerobic chamber at 35±2° C. for 5-7 days until clear colonies are observed. Count colonies using automated colony counter and calculate CFU/mL sample.

Results

Microbial Kill Time Assay: Planktonic *C. acnes* ATCC 11827, 10-Minute Treatment

| | Planktonic *C. acnes* ATCC 11827 (Average $Log_{10}$ Recovery) |
|---|---|
| Control (Untreated) | 5.0 |
| E1 (Inv.) | <2.7* (Below limit of detection) |
| E2 (Inv.) | <2.7* (Below limit of detection) |
| Placebo, pH 3.8 | 4.9 |
| Placebo, pH 4.5 | 4.8 |

As seen from the table above, Placebos 1-2 both exhibited almost the same bacteria counts as the untreated control. In contrast, the bacteria counts of inventive E1-2 were below the limit of detection. This demonstrates that E1-2 are effective in killing planktonic *C. acnes* bacteria. Furthermore, because E2 does not contain salicylic acid but still exhibited a high kill rate, the presence of the glycolic acid, gluconolactone and mandelic acid is surprisingly effective alone in killing planktonic *C. acnes* bacteria.

Example 3B: Effect on Biofilm

Bacteria in the biofilm state were treated with E1-2 and Placebos 1-2 and evaluated for effect. The protocols used are according to ASTM E2647-13: "Standard Test Method for Quantification of *Pseudomonas aeruginosa* Biofilm Grown Using Drip Flow Biofilm Reactor with Low Shear and Continuous Flow", and are also described below.

Preparation of *C. acnes* Biofilm

A standard *C. acnes* ATCC 11827 culture grown in Reinforced Clostridial Media (RCM) (Remel, Lenexa, KS) was used as the seed culture for biofilm formation. Biofilms were grown on halves of soda-lime glass microscope slides (VistaVision™, VWR International) in a growth medium of RCM supplemented with olive oil, oleic acid, and squalene. Biofilms were incubated anaerobically for 72±0.5 hours at 32.5±2.5° C.

Treatment of *C. acnes* Biofilm with Clear Skin Formulations:

After 72±0.5 hours, biofilms were removed from anaerobic conditions and treated with 1 gram of test product for 10 minutes. An untreated biofilm served as the negative control in each study. After treatment, the biofilm and test product were immediately scraped from slide halves and collected per ASTM E2647-13 (procedure modified to for *C. acnes* biofilm) into neutralizing broth (TAT Broth, Remel). After collection of the biofilm and test product into neutralizing broth (considered 100 dilution), serial dilutions were performed in 0.85% saline and plated onto Reinforced Clostridial Agar (RCA); plates were incubated anaerobically at 32.5±2.5° C. for 5-7 days. After incubation, colonies on plates were counted and average CFU/cm2 was calculated (representative of viability).

Results

*C. acnes* ATCC11827 Biofilm: 10-Minute Treatment Formulations

| | *C. acnes* ATCC 11827 Biofilm (Average $Log_{10}$ Recovery) |
|---|---|
| Control (Untreated) | 6.6 |
| E1 (Inv.) | 4.3 |
| E2 (Inv.) | 5.5 |

*C. acnes* ATCC11827 Biofilm: 10-Minute Treatment Formulations

| | *C. acnes* ATCC 11827 Biofilm (Average $Log_{10}$ Recovery) |
|---|---|
| Control (Untreated) | 6.7 |
| E1 (Inv.) | 4.3 |
| E2 (Inv.) | 5.4 |
| Placebo, pH 3.8 | 6.9 |
| Placebo, pH 4.5 | 6.6 |

As seen from the tables above, Placebos 1-2 both exhibited almost the same bacteria counts as the untreated control. In contrast, the bacteria counts of inventive E1-2 were much lower. This demonstrates that E1-2 are effective in killing *C. acnes* bacteria in the biofilm state. These results are surprising, as bacteria are known to be more difficult to kill when in biofilms. Furthermore, because E2 does not contain salicylic acid but still exhibited a high kill rate, the presence of the glycolic acid, gluconolactone and mandelic acid is effective alone in killing *C. acnes* bacteria in the biofilm state.

Example 3C: Biofilm Disruption Study

Disruption efficacy using formulations according to one or more embodiments of the invention was investigated against organism *Cutibacterium acnes* (*C. acnes*) ATCC 11827 in a biofilm state. Inventive composition (E1') was tested along with a placebo composition (Placebo 2, same as above) and a sterile water control treatment; all evaluated for the effect on *Cutibacterium acnes* (*C. acnes*) in a biofilm state. Placebo 2 is similar to E1' except the placebo composition does not contain propylene glycol, or any acids. Both the inventive composition (E1') and placebo composition (Placebo 2) have been pH adjusted to 3.8 to account for any pH effect. The breakdown of ingredients of the compositions are shown in the table below.

Compositions Used in Biofilm Disruption Assay Experiments

|  | E1' (Inv.) | Placebo 2 (Comp.) |
| --- | --- | --- |
| INCI | pH 3.8 | pH 3.8 |
| Water | 70.96 | 91 |
| Sodium Hydroxide | QS to pH 3.8 |  |
| Propylene Glycol | 5.0 |  |
| Glycolic Acid (70% active in water) | 7.14 |  |
| Gluconolactone | 2.45 |  |
| Mandelic Acid | 2.55 |  |
| Salicylic Acid | 0.5 |  |
| Hydroxyethyl Acrylate/Sodium Acryloyldimethyl Taurate Copolymer[1] | 1.4 | 1.4 |
| Polyacrylate Crosspolymer-6[2] | 1.0 | 1.0 |
| Dimethicone (and) Dimethicone Crosspolymer[3] | 4.5 | 4.5 |
| Misc. (Fragrance, chelating agent, skin conditioning agent etc.) | 2.1 | 2.1 |
| Citric Acid |  | Q.S. to 0.06 as needed |

*Cutibacterium acnes* bacteria in the biofilm state were treated with E1', Placebos 2 and sterile water control and evaluated for efficacy of biofilm disruption. The assays used are developed according to Holmberg, A. et al. "Biofilm Formation by *Propionacterium acnes* is a Characteristic of Invasive Isolates. Clin Microbiol Infect 2009; 15: 787-795.", which is described below.

Preparation of *C. acnes* Biofilm

A standard *C. acnes* ATCC 11827 culture grown in Reinforced Clostridial Media (RCM) (Remel, Lenexa, KS) was used as the seed culture for biofilm formation. Biofilms were grown in CoStar 96-well tissue culture-treated plates (Corning, Fisher Scientific, Pittsburgh, PA) in a growth medium of RCM supplemented with olive oil, oleic acid, and squalene. Biofilms were incubated in a 5% $CO_2$ atmosphere for 72±0.5 hours at 32.5±2.5° C.

Treatment of *C. acnes* Biofilm with Test Compositions:

After 72±0.5 hours, biofilms were removed from 5% $CO_2$ atmospheric conditions and treated for 30 seconds, static at room temperature with 200 μL of test compositions (E1' and Placebo 2, respectively) diluted 1:5 in sterile water. A biofilm treated with sterile water only served as the negative control in each study. After treatment, the biofilm and the test compositions were gently aspirated from the well then the wells were gently washed with 0.1% peptone water and dried ("fixed") for 60 minutes. After fixing, the biofilms were stained for 15-20 minutes with 1.0% crystal violet solution at room temperature. After staining, excess crystal violet solution was decanted and each well was gently rinsed with sterile water. Solvent (ethanol) was then added to each well for 30 minutes; solubilized dye was then aliquoted into a fresh 96-well plates and absorbance at optical density at 595 nm ($OD_{595\ nm}$) was measured because an average optical density at 595 nm ($OD_{595\ nm}$) is representative of biomass.

Results

Quantification of *C. acnes* Biofilm Disruption after Treatment with Test Compositions

| Test Composition | Average Biomass ($OD_{595\ nm}$) 30 seconds | Percentage of Biofilm Disruption (vs. Control) 30 seconds |
| --- | --- | --- |
| Control (Sterile Water) | 0.902 | N/A |
| E1' (Inv.) | 0.678 | 24.9 |
| Placebo 2 | 0.792 | 12.2 |

As seen from the table above, Control (Sterile Water) and Placebos 2 exhibited an average optical density (indicative of average biomass) at 0.902 and 0.792, respectively. In contrast, the Inventive E1' exhibited an average biomass at 0.678 which was much lower. This demonstrates that E1' is effective in disrupting *C. acnes* bacteria in the biofilm state. These results are surprising, as it is often difficult to disrupt the structure of a biofilm.

It will be understood that, while various aspects of the present disclosure have been illustrated and described by way of example, the invention claimed herein is not limited thereto, but may be otherwise variously embodied according to the scope of the claims presented in this and/or any derivative patent application.

The invention claimed is:

1. A method of treating acne, the method comprising contacting skin in need of such treatment with a composition comprising
   a. about 0.1 wt. % to about 7.5 wt. % glycolic acid;
   b. about 0.1 wt. % to about 5 wt. % gluconolactone;
   c. about 0.1 wt. % to about 5 wt. % mandelic acid
   d. a glycol;
   e. a salt-tolerant thickening polymer,
wherein the total amount of glycolic acid, gluconolactone and mandelic acid is less than about 15 wt. % of the total composition.

2. The method of claim 1, wherein the total amount of acid in the composition is less than about 15 wt. % of the total composition.

3. The method of claim 1, wherein the composition is left on the skin.

4. The method of claim 1, wherein the composition is in the form of a lotion.

5. The method of claim 1, wherein the composition has a pH of about 3 to about 5.

6. The method of claim 1, wherein the composition further comprises a glycol selected from the group consisting of glycerin, propylene glycol, butylene glycol, pentylene glycol, hexylene glycol, polyethylene glycol, polypropylene glycol, diethylene glycol, triethylene glycol, caprylyl glycol, glycerol, butanediol and hexanetriol, and copolymers and combinations thereof.

7. The method of claim 1, wherein the composition is substantially free of lactic acid.

8. The method of claim 1, wherein the composition is substantially free of salicylic acid.

9. The method of claim 1, wherein the salt-tolerant thickening polymer comprises a naturally-derived polymer or the salt-tolerant thickening polymer comprises a sulfonate group.

10. The method of claim 1, wherein the salt-tolerant thickening polymer is selected from the group consisting of polyacrylate crosspolymer-6, hydroxyethyl acrylate/sodium acryloyldimethyl taurate copolymer and combinations thereof.

* * * * *